United States Patent [19]
Chibata et al.

[11] 3,935,072
[45] Jan. 27, 1976

[54] PURIFICATION OF COENZYME A

[75] Inventors: Ichiro Chibata, Suita; Tetsuya Tosa, Kyoto; Yuhsi Matuo, Suita, all of Japan

[73] Assignee: Tanabe Seiyaku Co., Ltd., Osaka, Japan

[22] Filed: July 31, 1973

[21] Appl. No.: 384,212

[30] Foreign Application Priority Data

Aug. 10, 1972 Japan.............................. 47-80113
Aug. 10, 1972 Japan.............................. 47-80115

[52] U.S. Cl.................. 195/68; 195/63; 195/66 R; 195/DIG. 11; 260/112 R; 260/211.5 R
[51] Int. Cl.$^2$... C07G 7/02; C07G 7/00; C07G 3/00
[58] Field of Search....... 195/63, 68, DIG. 11, 66 R, 195/116; 260/212, 211.5, 112 R

[56] References Cited
UNITED STATES PATENTS

| | | | |
|---|---|---|---|
| 2,828,302 | 3/1958 | Mitz................................ | 260/211.5 |
| 3,645,852 | 2/1972 | Axen et al. ........................ | 195/63 X |
| 3,834,990 | 9/1974 | Werle et al. ...................... | 195/63 X |

OTHER PUBLICATIONS

Wilchek et al., Conversion of Protein Kinase to a Cyclic AMP Independent Form by Affinity Chromatography on Ne-Caproyl 3′,5′-Cyclic Adenosine Monophosphate-Seplharose. Biochemical and Biophysical Research Communications, Vol. 45, No. 5, 1971, (pp. 1177–1184).

Denburg et al., Purification of a Specific RNA by Sepharose -Round, Enzyme, Proceedings of the National Academy of Sciences, Vol. 67, No. 2, 1970, (pp. 1057–1062).

*Primary Examiner*—David M. Naff
*Attorney, Agent, or Firm*—Jordan G. Bierman; Linda B. Bierman; Kenneth J. Stempler

[57] ABSTRACT

Coenzyme A is purified by a process involving contacting a cyanogen halide-activated water-insoluble polysaccharide with a cell-free extract of a coenzyme A-producing microorganism to immobilize proteins such as enzymes having affinity for coenzyme A on the polysaccharide. The immobilized proteins are then contacted with a coenzyme A-containing solution to absorb coenzyme A followed by eluting coenzyme A from the immobilized proteins. Alternatively, the proteins having affinity for coenzyme A may be isolated from the cell-free extract prior to immobilization by absorbing the proteins on coenzyme A immobilized on a cyanogen halide-activated water-insoluble polysaccharide followed by eluting the proteins from the immobilized coenzyme A.

12 Claims, No Drawings

PURIFICATION OF COENZYME A

This invention relates to the purification of coenzyme A.

It is well known that coenzyme A (hereinafter referred to as "CoA") is an important compound in the metabolic processes of living cells. For example, it is useful in the metabolism of carbohydrates, fats and amino acids, and in the biosynthesis of protoheme IX.

Some methods for the purification of CoA are known. In one known method CoA is purified by treating a crude CoA solution with a heavy metal salt (e.g., mercuric, lead, silver or barium salt), phosphotungstic acid or an organic solvent, e.g., acetone (The Journal of Biological Chemistry 186, 253 – 243; ibid. 193, 307 – 316). In another method CoA is purified by a charcoal adsorption procedure or chromatography on the column of an ion exchange resin (The Journal of Americal Chemical Society 72, 4838; U.S. Pat. No. 2828302; Biochemistry 5, 3886 – 3886; Japanese Pat. Publication No. 10188/1965). However, all of these methods are disadvantageous in a commercial application because of insufficient purification of CoA and a great loss of CoA during the operations.

As a result of investigations, we have now found that a biologically specific interaction between CoA and its associated enzymes can be utilized advantageously for the purification of CoA. In other words, enzymes or proteins, which exhibit a special and unique affinity to CoA, are inherently contained in living cells of a CoA-producing microorganism. Such enzymes or proteins (i.e., "CoA-affinity-substance") can be advantageously used as a liquid which is coupled to a solid support for affinity chromatography. We have also found that the coupling of the ligand can be readily achieved by immobilizing the cell-free extract of a CoA-producing microorganism with a cyanogen halide-activated water-insoluble polysaccharide. Moreover, we have found that the aforementioned coupling can be achieved by separating CoA-affinity-substance from the cell-free extract of a CoA-producing microorganism by the use of an immobilized CoA, and then immobilizing the isolated CoA-affinity-substance with the cyanogen halide-activated water-insoluble polysaccharide. The resultant immobilized cell-free extract involving CoA-affinity-substance therein or the resultant immobilized CoA-affinity-substance is used as an adsorbed for the affinity chromatography of a crude CoA solution.

On object of the present invention is to provide a novel and practical method for treating a crude CoA solution to obtain a purified CoA solution. Another object of the invention is to provide a method for purfying CoA by affinity chromatography. The other object is to provide a method in which CoA is purified from a crude CoA solution by utilizing a biologically specific interaction between CoA and CoA-affinity-substance. A further object is to provide a method which enables the purification of CoA without substantial loss of CoA during the operation. Still further objects of the present invention will be apparent from the description which follows.

According to the present invention, a purified CoA solution is obtained by the steps of (a) immobilizing the cell-free extract of a CoA-producing microorganism with a cyanogen halide-activated water-insoluble polysaccharide to prepare an immobilized cell-free extract involving CoA-affinity-substance, (b) washing the immobilized cell-free extract, (c) contacting a crude CoA solution with the immobilized cell-free extract to have CoA adsorbed thereon, (d) washing the immobilized cell-free extract, and (e) eluting CoA from the immobilized cell-free extract. Alternatively, CoA-affinity-substance may be separated from the cell-free extract of a CoA-producing microorganism prior to the immobilization step mentioned to above. In this alternative method, the separation of CoA-affinity-substance is carried out by the steps of (a) immobilizing CoA with a cyanogen halide-activated water-insoluble polysaccharide, (b) contacting the resultant immobilized CoA with the cell-free extract of a CoA-producing microorganism to have CoA-affinity-substance absorbed on the immobilized CoA, and (c) eluting CoA-affinity-substance from the immobilized CoA. CoA-affinity-substance thus obtained is then immobilized with a cyanogen halide-activated water-insoluble polysaccharide. A purified CoA solution is obtained by contacting a crude CoA solution with the resultant immobilized CoA-affinity-substance to have CoA adsorbed thereon, washing the immobilized CoA-affinity-substance, and then eluting CoA from the immobilized CoA-affinity-substance.

The above-mentioned steps of the present invention are shown by the following scheme:

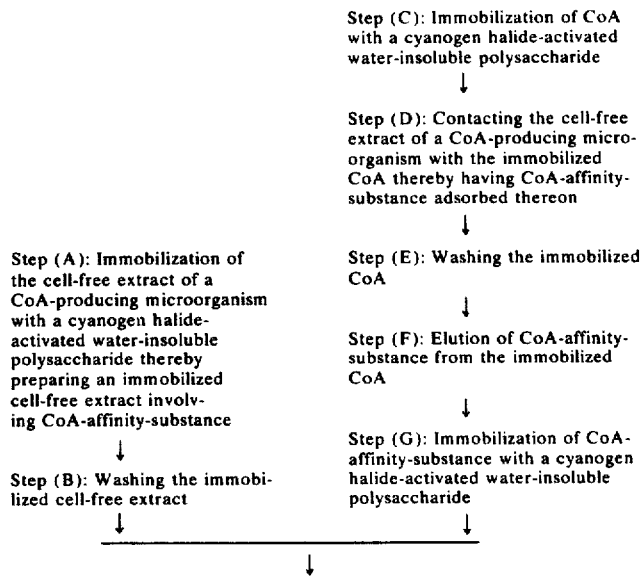

Step (H): Contacting a crude CoA solution with the immobilized cell-free extract of the immobilized CoA-affinity-substance thereby having CoA adsorbed on the immobilized preparation

↓

Step (I): Washing the immobilized preparation

↓

Step (J): Elution of CoA from the immobilized preparation

Mircroorganisms which produce CoA can be employed for the purpose of the present invention. Examples of the CoA-producing microorganisms include Sarcina lutea IAM (Institute of Applied Microbiology, Tokyo University, Japan) 1099, Sarcina aurantiaca IAM 1059, Sarcina aurantiaca IFO (Institute for Fermentation, Osaka, Japan) 3064, Micrococcus rubens IFO 3768, Mircrobacterium flavum IAM 1642, Brevibacterium ammoniagenes IAM 1641, Corynebacterium alkanophilum nov. sp. ATCC 21071 and Pseudomonas alkanolytica nov. sp. ATCC 21034. All of these microorganisms are publicly available from the above-mentioned depositories. In this connection, however, it should be noted that the present invention is not limited to the use of these specific microorganisms, but include within its scope the use of all CoA-producing microorganisms. The cell-free extract of each one of the above-mentioned microorganisms can be prepared by known methods such as, for example, homogenization, ultrasonic destruction or lysozyme treatment (c.f., Methods of Enzymology, Academic press Inc., New York, vol. 1, page 51 (1955)). Moreover, the cyanogen halide-activated water-insoluble polysaccharide of the invention can be prepared by known methods such as that disclosed in "Nature" 214, 1302 – 1304 (1967). The activation reaction of a water-insoluble polysaccharide (e.g., agarose, dextran, cellulose) with a cyanogen halide is shown by the following scheme:

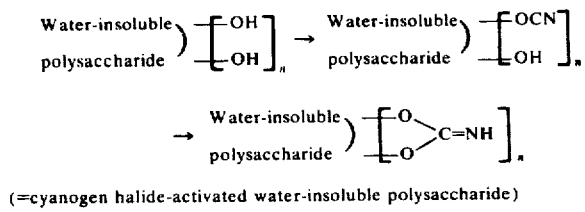

(=cyanogen halide-activated water-insoluble polysaccharide)

Suitable examples of said activated water-insoluble polysaccharide include cyanogen bromide-activated agarose, cyanogen chloride-activated agarose, cyanogen iodide-activated agarose, cyanogen bromide-activated dextran, cyanogen chloride-activated dextran, cyanogen iodide-activated dextran, cyanogen bromide-activated cellulose, cyanogen chloride activated-cellulose and cyanogen iodide-activated cellulose. In preparing the activated water-insoluble polysaccharide which is suitable for use in the present invention, it is preferred to use 0.01 to 0.05 mole, especially 0.01 to 0.03 mole, of a cyanogen halide per gram of the water-insoluble polysaccharide. For example, one to two grams of cyanogen bromide per gram of the water-insoluble polysaccharide are preferably used in the activation reaction.

Immobilization of the cell-free extract [i.e., Step (A)] in the present invention is readily accomplished by admixing the cell-free extract of CoA-producing microorganism with the cyanogen halide-activated water-insoluble polysaccharide at a pH of 6 to 9. It is preferred to carry out the reaction at 0° to 30°C, especially at 15° to 25°C, under stirring. The preferred amount of the cell-free extract which is used in the immobilization reaction is 10 to 30 mg, especially 15 to 20 mg, (based on the amount of protein) per gram of the cyanogen halide-activated water-insoluble polysaccharide. The immobilization reaction may be completed with 10 to 30 hours. The resultant immobilized cell-free extract involving CoA-affinity-substance is then washed with a solvent until materials which are not covalently bound to the activated water-insoluble polysaccharide are removed. Water and an aqueous sodium chloride solution (pH 6 – 8) are employed as the washing solvent.

Immobilization of CoA [i.e., Step (C)] is accomplished by admixing CoA with the cyanogen halide-activated water-insoluble polysaccharide at a pH of 6 to 8. The immobilization reaction is carried out at 0° to 30°C, especially at 15° to 25°C, under stirring. Moreover, in this immobilization reaction it is preferred to use a highly purified CoA, especially an authentic sample of the reduced CoA. The immobilization reaction of CoA may be completed within 6 to 10 hours. The preferred amount of the reduced CoA which is bound to the activated water-insoluble polysaccharide is 2 to 5 mg, especially 3 to 4 mg, per gram of the activated water-insoluble polysaccharide. For the immobilization reaction, therefore, it is preferred to use 2 to 10 mg of the reduced CoA per gram of the activated water-insoluble polysaccharide. The immobilized reduced CoA thus obtained is represented by the following formula:

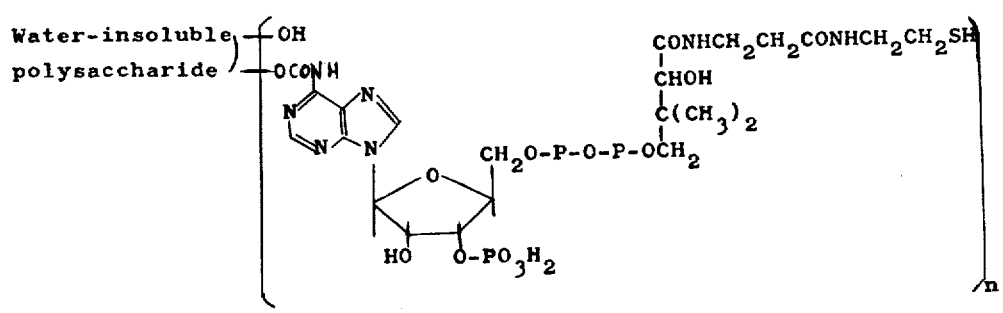

In carrying out the adsorption procedure [i.e., Step (D)] it is preferred to use the cell-free extract having an ionic strength lower than 0.1, especially an ionic strength of 0.05 to 0.1. When the cell-free extract prepared from the CoA-producing microorganism shows an ionic strength higher than 0.1, it is recommended to dialyze said extract against water prior to the adsorption procedure of Step (D). On the other hand, when the cell-free extract shows an ionic strength lower than 0.05, an insert electrolyte such as sodium chloride may be added to the cell-free extract so that the ionic strength thereof is adjusted to 0.05 to 0.1. The cell-free extract adjusted as above is then mixed with the immobilized CoA, and the mixture is stirred at 0° to 30°C, especially at 15° to 25°C. Then, the mixture is filtered and the immobilized CoA thus recovered is further washed with an aqueous solution (pH 6 – 8) having an ionic strength of 0.05 to 0.1. Examples of the washing solvent which is used in Step (E) include an aqueous 0.01 M sodium acetate buffer solution (pH 6.5) containing 0.05 M sodium chloride, and an aqueous 0.01 M phosphate buffer solution (pH 7.0) containing 0.05 M sodium chloride. By these operations the immobilized CoA having adsorbed CoA-affinity-substance thereon is obtained. Alternatively, the adsorption and its subsequent procedures [i.e., Steps (D) to (F)] of the invention may be carried out by a column method. For example, the immobilized CoA obtained in Step (C) is charged into a column, and the cell-free extract (pH 6 – 8) adjusted as above is passed through the column at 0° to 30°C, especially at 15° to 25°C. By washing the column with such an aqueous solution as mentioned above, the immobilized CoA having adsorbed CoA-affinity-substance thereon is obtained.

Elution of CoA-affinity-substance from the immobilized CoA, i.e., Step (F), is readily accomplished. As the eluting solvent there is used an aqueous solution (pH 6 – 8) having an ionic strength higher than 0.5, especially an ionic strength of 0.5 to 1. For example, an aqueous 0.01 M sodium acetate buffer solution (pH 6.5) containing 0.5 M sodium chloride, and an aqueous 0.1 M phosphate buffer solution (pH 7.0) containing 0.2 M sodium chloride are suitably employed as the eluting solvent. It is preferred to carry out the elution at 0° to 30°C, especially at 15° to 25°C. Immobilization of CoA-affinity-substance thus eluted, i.e., Step (G), can be carried out in the same manner as described in Step (A). The preferred amount of CoA-affinity-substance which is used in the immobilization reaction of Step (G) is 10 to 30 mg, especially 15 to 20 mg, (based on the amount of protein) per gram of the cyanogen halide-activated water-insoluble polysaccharide.

The immobilized cell-free extract or CoA-affinity-substance obtained in Steps (B) or (G) is then contacted with a crude CoA solution to have CoA adsorbed on the immobilized preparation. That is, the immobilized cell-free extract or CoA-affinity-substance is mixed with the crude CoA solution, and the mixture is stirred. After filtering the mixture, the immobilized preparation recovered is further washed with a suitable solvent. By these operations, the immobilized cell-free extract or CoA-affinity-substance having adsorbed CoA thereon is obtained. Alternatively, the adsorption and its subsequent procedures [i.e., Steps (H) to (J)] may be carried out by a column method. For example, the immobilized preparation obtained in Steps (B) or (G) is charged into a column, and a crude CoA solution is passed through the column at a suitable flow rate. By washing the column with a suitable solvent, the immobilized cell-free extract or CoA-affinity-substance having adsorbed CoA thereon is obtained. The adsorption procedure, i.e., Step (H), is preferably carried out at a pH of 6 to 8 and at 0° to 30°C, especially at 15° to 25°C. Moreover, as the washing solvent in Step (I) there is used an aqueous solution (pH 6 – 8) having an ionic strength lower than 0.04, especially an ionic strength of 0.02 to 0.04. Examples of the washing solvent which are employed in Step (I) include an aqueous 0.01 M sodium acetate buffer solution (pH 6.5) containing 0.03 M sodium chloride, and an aqueous 0.005 M phosphate buffer solution (pH 7.0) containing 0.02 M sodium chloride.

Elution of CoA from the resultant immobilized cell-free extract or CoA-affinity-substance, i.e., Step (J), is preferably carried out at 0° to 30°C, especially at 15° to 25°C. An aqueous acidic solution (pH 2 – 5) is employed as the eluting solvent in this step. Moreover, an aqueous solution (pH 6 – 8) having an ionic strength higher than 0.06, especially an ionic strength of 0.1 to 0.5 is employed as the eluting solvent which is used in Step (J) include an aqueous 0.01 M sodium acetate buffer solution (pH 6.5) containing 0.1 M sodium chloride, and an aqueous 0.01 M phosphate buffer solution (pH 7.0) containing 0.06 M sodium chloride. When the elution is completed, the immobilized cell-free extract or CoA-affinity-substance is recovered as a solid material. The immobilized preparation thus recovered can be used repeatedly for the purpose of the present invention.

According to the above-mentioned method of the present invention, a CoA extract which is obtained from animal tissues (e.g., hog livers) or the fermentation broth of a CoA-producing microorganism can be readily purified. Moreover, a supernatant solution or filtrate which is obtained by centrifuging or filtering the heat-treated fermentation broth of a CoA-producing microorganism may be employed as the crude CoA solution of the present invention. A CoA solution which is obtained by purifying said supernatant solution or filtrate with an active charcoal may also be employed as the crude CoA-solution of the invention. Alternatively, the CoA solution purified with the active charcoal as mentioned above may be further purified by chromatography on a column of an ion exchange resin such as DEAE-cellulose prior to the purification of the present invention.

Practical and presently-preferred embodiments of the present invention are illustratively shown in the following Examples. In this specification, the amount of CoA (i.e., the total amount of the reduced and oxidized CoA) was assayed in the presence of cysteine by the phosphotransacetylase method described in "The Journal of Biological Chemistry" 191, 365 (1951). The amount of the reduced CoA was also assayed spectrophotometrically by the phosphotransacetylase method described in "Methods of Enzymatic Analysis" page 512 (1963, Academic Press Incorp.). The purity (%) of each of CoA and the reduced CoA was estimated in accordance with the following equation:

$$\text{Purity}(\%) \text{ of CoA} = \left[\frac{\text{The amount of CoA (i.e., total amount of the reduced and oxidized CoA) assayed by the above-mentioned method}}{\text{The amount of CoA (i.e., total amount of the reduced and oxidized CoA) calculated from the absorbance at 257 nm}}\right] \times 100$$

$$\text{Purity}(\%) \text{ of the reduced CoA} = \left[\frac{\text{Amount of the reduced CoA assayed by the above-mentioned method}}{\text{Amount of the reduced CoA calculated from the absorbance at 257 nm}}\right] \times 100$$

Moreover, the amount of CoA-affinity-substance was measured in accordance with the method described in "The Journal of Biological Chemistry" 198, 265 (1951). Further, in this specification and claims, the terminology "CoA(or coenzyme A)-affinity-substance" should be interpreted as referring to "a group of enzymes or proteins being inherently contained in living cells of a CoA(or coenzyme A)-producing microorganism and at the same time being adsorbed to CoA(or coenzyme A) in an aqueous solution (pH 6 - 8) having an ionic strength lower than 0.1". More specifically, for example, the terminology "CoA(or coenzyme A)-affinity-substance" refers to "a mixture of enzymes or proteins selected from the group consisting of dephospho-CoA(or coenzyme A) kinase, acyltransferase, acyl-CoA(or coenzyme A) reductase, palmitoyl-CoA(or coenzyme A) hydrolase, succinyl-CoA(or coenzyme A) hydrolase, citrate synthase and other analogeous proteins having affinity to CoA".

EXAMPLE 1

1. Preparation of the cell-free extract of a CoA-producing microorganism 10 liters of an aqueous nutrient medium containing glucose (10 w/v %), corn steep liquor (2.2 w/v %), peptone (1.35 w/v %), monopotassium phosphate (0.5 w/v %), dipotassium phosphate (0.5 w/v %), magnesium sulfate 7 hydrate (0.1 w/v %), ammonium acetate (1.0 w/v %) and biotin (0.05 µg/ml) are charged into a jar fermentor. The nutrient medium is adjusted to pH 7.0 and then sterilized. *Sarcina lutea* IAM 1099 is inoculated into the nutrient medium. The medium is then cultivated at 30°C for 72 hours under aeration (3 liters/minute) and agitation (350 rotations/minute). The fermentation broth thus obtained is centrifuged. The microbial cells thus collected are lyophilized, whereby 500 g of the lyophilized cells of *Sarcina lutea* IAM 1099 are obtained. 100 g of the lyophilized cells are suspended in 3.5 liters of a 0.05 M phosphate buffer solution (pH 7.0). The suspension is subjected to ultrasonic treatment (20 kilocycles/hour) under ice-cooling and then to centrifugation. 3 liters of the cell-free extract of *Sarcina lutea* IAM 1099 are obtained.

2. Preparation of a cyanogen halide-activated water-insoluble polysaccharide 700 g of agarose (wet form) (manufactured by Pharmacia Fine Chemical Co. under the trade name "Sepharose") are suspended in 28 liters of an aqueous cyanogen bromide solution (Contents of cyanogen bromide: 25 mg/ml), and the suspension is stirred at about 25°C for 8 minutes. The suspension is kept at pH 11 with an aqueous 5N-sodium hydroxide solution during the reaction. After the reaction, the resultant precipitate is collected by filtration. The precipitate thus collected is washed with water and an aqueous 0.1 M sodium bicarbonate solution. 650 g of cyanogen bromide-activated agarose (wet form) are obtained.

3. Preparation of an immobilized cell-free extract 320 g of cyanogen bromide-activated agarose (wet form) are added to 3 liters of the cell-free extract obtained in the above-mentioned paragraph (1). After the mixture is stirred at 10°C for 17 hours, 320 g of cyanogen bromide-activated agarose (wet form) are again added thereto. Then, the mixture is adjusted to pH 6.0 and is further stirred at 10°C for 6 hours. The resultant precipitate is collected by filtration. The precipitate thus collected is washed with water and an aqueous 0.01 M sodium acetate solution (pH 7.0). 640 g of an immobilized cell-free extract (wet form) are obtained.

4. Purification of CoA

A seed culture is prepared by cultivating *Sarcina lutea* IAM 1099 for 20 hours in an aqueous medium containing the same ingredients as described in the above-mentioned paragraph (1). 20 ml of an aqueous nutrient medium containing the same ingredients as described in said paragraph (1) are charged into a 500 ml shaking flask, and 0.5 ml of the seed culture is added thereto. The nutrient medium is cultivated at 30°C for 48 hours under shaking (140 rotations/minute). 20 mg of potassium panthotenate, 20 mg of adenine and 20 mg of cystein hydrochloride are dissolved in the nutrient medium, and the medium is diluted with water to bring its volume to 25 ml. Then, the medium is further cultivated at 30°C for 16 hours under shaking (140 rotations/minute). The fermentation broth thus obtained is heated at 100°C for 10 minutes and then is centrifuged. 340 ml of water are added to the supernatant solution, whereby 510 ml of a crude CoA solution (pH 6.5, ionic strength = 0.04) are obtained. The solution contains 94 mg of CoA (purity: 0.7 %).

640 g of the immobilized cell-free extract obtained in the above-mentioned paragraph (3) are charged into a 5 cm × 50 cm column, and the column is washed with an aqueous 0.01 M sodium acetate solution (pH 6.5). 510 ml of the crude CoA solution thus obtained are passed through the column at a flow rate of 18 ml/hour. The column is washed with an aqueous 0.01 mol solution acetate buffer solution (pH 6.5) containing 0.03 M sodium chloride until contaminants are removed from the column. Then, an aqueous 0.01 M sodium acetate buffer solution (pH 6.5) containing 0.5 mol sodium chloride is passed through the column to elute CoA therefrom. The eluate thus obtained contains 59 mg of CoA (purity: 71 %).

EXAMPLE 2

*Sarcina lutea* IAM 1099 is cultivated in the same manner as described in Example 1, paragraph (4). The fermentation broth obtained is heated at 100°C for 10 minutes and filtered by centrifugation. One liter of the supernatant solution thus obtained is introduced into a column of 10 g of active charcoal to have CoA adsorbed on the column. After washing the column with water a mixture of aqueous acetone and aqueous ammonia (an aqueous 40 % acetone solution : an aqueous 28 % ammonia solution = 100 : 1) is passed through the column. The eluates containing CoA are collected, combined and concentrated under reduced pressure to bring its volume to 100 ml. 15 ml of 2-mercaptoethanol are added to 100 ml of the concentrated eluate. Then, the mixture is adjusted to approximately pH 8. After the mixture is stirred for about 2 hours, 1.2 liters of ethanol are added thereto. The resultant precipitate is collected by centrifugation and then dissolved in water. 35 ml of a crude CoA solution are obtained. The solution contains 316 mg of CoA (purity: 13 %).

640 g of an immobilized cell-free extract prepared in the same manner as described in Example 1, paragraph (3), are charged in a 5 cm × 50 cm column. The column is washed with an aqueous 0.01 M sodium acetate solution (pH 6.5). 8 ml of the crude CoA solution obtained above are diluted with 72 ml of water, and passed through the column at a flow rate of 18 ml/hr. Then, the column is treated in the same manner as described in Example 1, paragraph (4). The eluate thus obtained contains 60 mg of CoA (purity: 100 %).

EXAMPLE 3

1. Preparation of the cell-free extract of a CoA-producing microorganism 10 liters of an aqueous nutrient medium containing glucose (5 w/v %), corn steep liquor (2.2 w/v %), peptone (1.4 w/v %), monopotassium phosphate (0.5 w/v %), dipotassium phosphate (0.5 w/v %) and magnesium sulfate 7 hydrate (0.1 w/v %) are charged into a jar fermentor. The nutrient medium is adjusted to pH 7.0 and then sterilized. After *Microbacterium flavum* IAM 1642 is inoculated into the nutrient medium, the medium is treated in the same manner as described in Example 1, paragraph (1). Thus, 2.6 liters of the cell-free extract of *Microbacterium flavum* IAM 1642 are obtained.

2. Preparation of an immobilized cell-free extract 1.5 kg of cyanogen bromide-activated agarose prepared in the same manner as described in Example 1, paragraph (2), are added to 2.6 liters of the cell-free extract of *Microbacterium flavum* IAM 1642 obtained above. Then, the mixture is treated in the same manner as described in Example 1, paragraph (3). 1.5 kg of an immobilized cell-free extract are obtained.

3. Purification of CoA 1.5 kg of the immobilized cell-free extract obtained above are charged in a 10 cm × 30 cm column. The column is washed with an aqueous 0.01 M sodium acetate solution (pH 6.5). 11 ml of a crude CoA solution prepared in the same manner as described in Example 2 are diluted with water to bring its volume to 110 ml, and the diluted CoA solution (CoA content: 99 mg, purity: 13 %) is passed through the column at a flow rate of 18 ml/hr. Then, the column is treated in the same manner as described in Example 1, paragraph (4). The eluate thus obtained contains 94 mg of CoA (purity: 73 %).

EXAMPLE 4

1. Preparation of the cell-free extract of a CoA-producing microorganism 10 liters of an aqueous nutrient medium containing glucose (5 w/v %), meat extract (1 w/v %), yeast extract (0.45 w/v %), protein hydrolysate (0.55 w/v %), peptone (1.35 w/v %), monopotassium phosphate (0.5 w/v %), dipotassium phosphate (0.5 w/v %) and magnesium sulfate 7 hydrate (0.1 w/v %) are charged into a jar fermentor. The nutrient medium is adjusted to pH 7.0 and then sterilized. After *Micrococcus rubens* IFO 3768 is inoculated into the nutrient medium, the medium is treated in the same manner as described in Example 1, paragraph (1). Thus, 3.3 liters of the cell-free extract of *Micrococcus rubens* IFO 3768 are obtained.

2. Preparation of an immobilized cell-free extract 3.65 kg of cyanogen bromide-activated agarose (wet form) prepared in the same manner as described in Example 1, paragraph (2), are added to 3.3 liters of the cell-free extract of *Micrococcus rubens* IFO 3768 mentioned to above. The mixture is then treated in the same manner as described in Example 1, paragraph (3). 3.65 kg of an immobilized cell-free extract are obtained.

3. Purification of CoA 3.65 kg of the immobilized cell-free extract mentioned above are charged into a 10 cm × 75 cm column. The column is washed with an aqueous 0.01 M sodium acetate solution. 15 ml of a crude CoA solution prepared in the same manner as described in Example 2 are diluted with 135 ml of water, and the diluted crude CoA solution (CoA content: 135 mg, purity: 13 %) is passed through the column at a flow rate of 18 ml/hour. The column is washed with an aqueous 0.01 M sodium acetate buffer solution (pH 6.5) containing 0.04 M sodium chloride until contaminants are removed from the column. The column is then treated in the same manner as described in Example 1, paragraph (4). The eluate thus obtained contains 126 mg of CoA (purity: 76 %).

EXAMPLE 5

1. Preparation of the cell-free extract of a CoA-producing microorganism 10 liters of an aqueous nutrient medium containing glucose (1 w/v %), peptone (1.5 w/v %), yeast extract (0.1 w/v %), dipotassium phosphate (0.3 w/v %), sodium chloride (0.2 w/v %) and magnesium sulfate 7 hydrate (0.02 w/v %) are charged in a jar fermentor. The nutrient medium is adjusted to pH 7.0 and then sterilized. After *Brevibacterium ammoniagenes* IAM 1641 is inoculated into the nutrient medium, the medium is treated in the same manner as described in Example 1, paragraph (1). Thus, 1.3 liters of the cell-free extract of *Brevibacterium ammoniagenes* IAM 1641 are obtained.

2. Preparation of an immobilized cell-free extract 1.3 kg of cyanogen bromide-activated agarose (wet form) prepared in the same manner as described in Example 1, paragraph (2), are added to 1.3 liters of the cell-free extract of *Brevibacterium ammoniagenes* IAM 1641 mentioned to above. Then, the mixture is treated in the same manner as described in Example 1, paragraph (3). 1.3 kg of an immobilized cell-free extract are obtained.

3. Purification of CoA 1.3 kg of the immobilized cell-free extract mentioned above are suspended in one liter of an aqueous 0.01 mol sodium acetate solution (pH 7.0). 4 ml of a crude CoA solution (CoA content: 36 mg, purity: 13 %) prepared in the same manner as described in Example 2 are added to the suspension. The mixture is stirred at room temperature for 5 hours thereby adsorbing CoA on the immobilized cell-free extract. The immobilized cell-free extract is collected by filtration and washed with an aqueous 0.01 M sodium acetate solution (pH 7.0) containing 0.01 M sodium chloride until contaminants are removed from the immobilized preparation. The immobilized cell-free extract is then suspended in 1.7 liters of an aqueous 0.01 M sodium acetate solution (pH 7.0) containing 0.5 M sodium chloride. The suspension is stirring at room temperature for 2 hours. Next, the suspension is filtered to remove insoluble materials. The filtrate thus obtained contains 23 mg of CoA (purity: 70 %).

EXAMPLE 6

1. Preparation of an immobilized CoA 510 g of the cyanogen bromide-activated agarose mentioned above are suspended in one liter of an aqueous 0.1 mol sodium acetate buffer solution (pH 6.0), and 0.6 g of the reduced CoA (purity: 92 %) is added thereto. The suspension is stirred at room temperature for 3 hours. The resultant precipitate is collected by filtration. The precipitate thus collected is washed with water and an aqueous 0.5 mol sodium chloride solution. 500 g of an immobilized CoA are obtained. It contains 3 mg of the reduced CoA per g. Moreover, it is positive to a nitroprusside reaction and shows an infrared adsorption band at 1720 cm$^{-1}$ to (R—O—CON=).

2. Preparation of CoA-affinity-substance 500 g of the immobilized CoA obtained in paragraph (1) are charged in a 5 cm × 40 cm column. The column is washed with an aqueous 0.1 M sodium chloride. The cell-free extract of *Sarcina lutea* IAM 1099 prepared in the same manner as described in Example 1, paragraph (1), is dialyzed at 1°C overnight through cellophan against water, and 850 ml of the dialyzed solution is passed through the column. The column is washed with an aqueous 0.01 M sodium acetate buffer solution (pH 6.5) containing 0.1 M sodium chloride until contaminants are removed from the column. Then, the column is eluted with an aqueous 0.01 M sodium acetate buffer solution (pH 6.5) containing 0.5 M sodium chloride. 3 liters of the eluate thus obtained contain 3.5 g of CoA-affinity-substance.

3. Preparation of an immobilized CoA-affinity-substance 270 g of cyanogen bromide-activated agarose (wet form) prepared in the same manner as described in Example 1, paragraph (2) are added to 3 liters of the eluate obtained in paragraph (2). After the mixture is stirred at 10°C for 17 hours, 270 g of cyanogen bromide-activated agarose (wet form) obtained in paragraph (1) are again added thereto. Then, the mixture is adjusted to pH 6.0 and further stirred at 10°C for 6 hours. The resultant precipitate is collected by filtration. The precipitate thus collected is washed with an aqueous 0.01 M sodium acetate buffer solution (pH 7.0) containing one M sodium chloride. 530 g of an immobilized CoA-affinity-substance (wet form) are obtained.

4. Purification of CoA 530 g of the immobilized CoA-affinity-substance (wet from) obtained in paragraph (3) mentioned to above are charged in a 5 cm × 43 cm column. The column is washed with an aqueous 0.01 sodium acetate buffer solution (pH 6.5) containing 0.01 M 2-mercaptoethanol. 6 ml of a crude CoA solution prepared in the same manner as described in Example 2 are diluted with 72 ml of water, and passed through the column at a flow rate of 18 ml/hour. The column is washed with an aqueous 0.01 M sodium acetate buffer solution (ph 6.5) containing 0.03 M sodium chloride until contaminants are removed from the column. Then, the column is eluted with an aqueous 0.01 M sodium acetate buffer solution (pH 6.5) containing 0.5 M sodium chloride. The eluate thus obtained contains 50 mg of the reduced CoA (purity: 98 %).

EXAMPLE 7

An immobilized CoA-affinity-substance is prepared in the same manner as described in Example 6, paragraph (3). One kg of the immobilized CoA-affinity-substance is washed with water and then suspended in 2 liters of an aqueous 0.01 M sodium acetate solution. 12 ml of a crude CoA solution prepared in the same manner as described in Example 2 are added to the suspension. The suspension is stirred at room temperature for 5 hours. The resultant precipitate is collected by filtration. The precipitate thus collected is washed with an aqueous 0.01 M sodium acetate buffer solution (pH 7.0) containing 0.03 M sodium chloride until contaminants are removed from the precipitate. Then, the precipitate is suspended in 1.3 liters of an aqueous 0.01 M sodium acetate solution (pH 7.0) containing 0.5 mol sodium chloride. After the suspension is stirred at room temperature for 2 hours, the resultant precipitate is removed by filtration. The filtrate thus obtained contains 81 mg of the reduced CoA (purity: 98 %).

What we claim is:

1. A process for purifying coenzyme A which comprises the steps of:
    A. admixing a cell-free extract of a coenzyme A-producing microorganism with a cyanogen halide-activated water-insoluble polysaccharide at a pH of 6 to 9 thereby immobilizing proteins contained in the extract; and washing the immobilized proteins until materials which are not covalently bound thereto are removed; or
    B. admixing coenzyme A with a cyanogen halide-activated water-insoluble polysaccharide at a pH of 6 to 8 to give an immobilized coenzyme A; contacting the immobilized coenzyme A with a cell-free extract of a coenzyme A-producing microorganism at a pH of 6 to 8, said extract having an ionic strength of 0.05 to 0.1, whereby proteins which exhibit special and unique affinity to coenzyme A and are inherently contained in living cells of the coenzyme A-producing microorganism are adsorbed on the immobilized coenzyme A; washing the immobilized coenzyme A with an aqueous solution of pH 6 to 8 having an ionic strength of 0.05 to 0.1; contacting the washed immobilized coenzyme A with an aqueous solution of pH 6 to 8 having an ionic strength higher than 0.5 to elute the proteins from the immobilized coenzyme A; and admixing the resultant proteins with a cyanogen halide-activated water-insoluble polysaccharide at a pH of 6 to 9 to give immobilized proteins; and C. contacting a coenzyme A solution with the immobilized proteins or enzymes at a pH of 6 to 8 to have coenzyme A adsorbed on the immobilized preparation; washing the immobilized proteins with an aqueous solution of pH 6 to 8 having an ionic strength lower than 0.4; and then contacting the washed immobilized proteins with an aqueous acidic solution of pH 2 to 5 or with an aqueous solution of pH 6 to 8 having an ionic strength aqueous solution of pH 6 to 8 having an ionic strength of 0.1 to 0.5, at 0° to 30°C, to elute coenzyme A from the immobilized preparation.

2. The process of claim 1 wherein the proteins are enzymes.

3. A process for purifying coenzyme A which comprises the steps of admixing a cell-free extract of a coenzyme A-producing microorganism with a cyanogen halide-activated water-insoluble polysaccharide at a pH of 6 to 9 at 0° to 30°C thereby immobilizing proteins contained in the extract; washing the immobilized proteins with water or an aqueous sodium chloride solution of pH 6 to 8, or both, until materials which are not covalently bound thereto are removed; contacting a coenzyme A solution with the immobilized proteins at a pH of 6 to 8 at 0° to 30°C to have coenzyme A adsorbed on the immobilized preparation; washing the resultant immobilized proteins with an aqueous solution of pH 6 to 8 having an ionic strength of 0.04 to 0.02; and then contacting the washed immobilized proteins with an and are inherently contained in living cells of the coenzyme A-producing microorganism are adsorbed on the immobilized coenzyme A; washing the immobilized coenzyme A with an aqueous solution of pH 6 to 8 having an ionic strength of 0.05 to 0.1; contacting the immobilizing coenzyme A with an aqueous solution of pH 6 to 8 having an ionic strength of 0.5 to 0.1, at 0° to 30°c, to elute the proteins from the immobilized coenzyme A; admixing the resultant proteins with a cyanogen halide-activated water-insoluble polysaccharide at a pH of 6 to 8 at 0° to 30°C to give an immobilized protein; contacting a coenzyme A solution with the immobilized proteins at a pH of 6 to 8 at 0° to 30°C to have coenzyme A adsorbed on the immobilized preparation; washing the immobilized proteins with an aqueous solution of pH 6 to 8 having an ionic strength of 0.02 to 0.04; and then contacting the washed immobilized proteins with and aqueous solution of pH 6 to 8 having an ionic strength of 0.1 to 0.5, at 0° to 30°C, to elute coenzyme A from the immobilized preparation.

4. The process according to claim 3, in which the immobilization of the proteins is carried out by admixing 10 to 30 mg based on the amount of protein of the cell-free extract of the coenzyme A-producing microorganism per gram of the cyanogen halide-activated water-insoluble polysaccharide.

5. The process according to claim 3, in which the temperature is adjusted to 15° to 25°C during the steps.

6. The process according to claim 3, in which the cyanogen halide-activated water-insoluble polysaccharide is selected from the group consisting of cyanogen bromide-activated agarose, cyanogen chloride-activated agarose, cyanogen iodide-activated agarose, cyanogen bromide-activated dextran, cyanogen chloride-activated dextran, cyanogen iodide-activated dextran, cyanogen bromide-activated cellulose, cyanogen chloride-activated cellulose and cyanogen iodide-activated cellulose.

7. A process for purifying coenzyme A which comprises the steps of admixing coenzyme A with a cyanogen halide-activated water-insoluble polysaccharide at a pH of 6 to 8 at 0° to 30°C to give an immobilized coenzyme A; contacting the immobilized coenzyme A with the cell-free extract of a coenzyme A-producing microorganism at a pH of 6 to 8 at 0° to 30°C, said extract having an ionic strength of 0.05 to 0.1 whereby proteins which exhibit special and unique affinity to coenzyme A higher than 0.06 to elute coenzyme A from the immobilized preparation.

8. The process according to claim 7, in which the immobilized proteins are prepared by admixing 10 to 30 mg protein per gram of the cyanogen halide-activated water-insoluble polysaccharide.

9. The process according to claim 7, in which the immobilized proteins are prepared by admixing 15 to 20 mg protein per gram of the cyanogen halide-activated water-insoluble polysaccharide.

10. The process according to claim 7, in which the immobilized coenzyme A is prepared by admixing 2 to 10 mg of coenzyme A per gram of the cyanogen halide-activated water-insoluble polysaccharide.

11. The process according to claim 7, in which the temperature is adjusted to 15° to 25°C during the steps.

12. The process according to claim 7, in which the cyanogen halide-activated water-insoluble polysaccharide is selected from the group consisting of cyanogen bromide-activated agarose, cyanogen chloride-activated agarose, cyanogen iodide-activated agarose, cyanogen bromide-activated dextran, cyanogen chloride-activated dextran, cyanogen iodide-activated dextran, cyanogen bromide-activated cellulose, cyanogen chloride-activated cellulose and cyanogen iodide-activated cellulose.

* * * * *